(12) United States Patent
Kaar et al.

(10) Patent No.: US 10,105,502 B2
(45) Date of Patent: Oct. 23, 2018

(54) DOSE COUNTER FOR A METERED-DOSE INHALER

(75) Inventors: Simon G. Kaar, Cork (IE); Jeffrey A. Karg, Hopkinton, MA (US); Timothy Norman Johnson, Raymond, NH (US); Robert Charles Uschold, Leominster, MA (US)

(73) Assignee: IVAX INTERNATIONAL B.V., Utrecht (NL)

(*) Notice: Subject to any disclaimer, the term of this patent is extended or adjusted under 35 U.S.C. 154(b) by 979 days.

(21) Appl. No.: 13/387,532

(22) PCT Filed: Jul. 28, 2010

(86) PCT No.: PCT/EP2010/004791
§ 371 (c)(1),
(2), (4) Date: Jun. 8, 2012

(87) PCT Pub. No.: WO2011/012326
PCT Pub. Date: Feb. 3, 2011

(65) Prior Publication Data
US 2012/0240925 A1    Sep. 27, 2012

Related U.S. Application Data

(60) Provisional application No. 61/229,830, filed on Jul. 30, 2009.

(51) Int. Cl.
| A61M 15/00 | (2006.01) |
| G06M 1/04 | (2006.01) |
| G06M 1/24 | (2006.01) |

(52) U.S. Cl.
CPC ...... *A61M 15/0078* (2014.02); *A61M 15/009* (2013.01); *G06M 1/04* (2013.01);
(Continued)

(58) Field of Classification Search
CPC ............ A61M 15/009; A61M 15/0068; A61M 15/0071; A61M 15/0073; A61M 15/0075; A61M 15/0076; A61M 15/0078
(Continued)

(56) References Cited

U.S. PATENT DOCUMENTS 5,349,945 A * 9/1994 Wass .................. A61M 15/009
128/200.14
6,142,339 A * 11/2000 Blacker ............... A61M 15/009
128/200.23
(Continued)

FOREIGN PATENT DOCUMENTS

| CN | 1265601 A | 9/2000 |
| CN | 1946448 A | 4/2007 |
(Continued)

OTHER PUBLICATIONS

International Search Report, dated Nov. 4, 2010, International Appl. No. PCT/EP2010/004790, filed Jul. 28, 2010, IVAX Pharmaceuticals Ireland.
(Continued)

*Primary Examiner* — Gregory Anderson
*Assistant Examiner* — Elliot S Ruddie
(74) *Attorney, Agent, or Firm* — Morgan, Lewis & Bockius LLP (57) ABSTRACT

A dose counter for counting does of medicament dispensed by or remaining in a metered-dose inhaler. The dose counter includes a rotatably mounted gear wheel having a circular arrangement of ratchet teeth defining a root circle and a display coupled to the gear wheel, the display having a visible array of dose counting indicia indexable in response to rotary motion of the gear wheel. The dose counter further includes an actuator mechanism having a driver for rotatably driving the gear wheel in response to the dispensation of a
(Continued)

medicament dose, the driver being arranged to engage the ratchet teeth of the gear wheel. The actuator mechanism includes an actuator shaft mounted for linear movement in response to the dispensing of a dose of medicament. In use, the travel of the driver along the root circle of the gear wheel exceeds the corresponding linear movement of the actuator shaft.

20 Claims, 8 Drawing Sheets

(52) U.S. Cl.
CPC ..... *A61M 15/0073* (2014.02); *A61M 15/0075* (2014.02); *A61M 2202/064* (2013.01); *G06M 1/041* (2013.01); *G06M 1/24* (2013.01)

(58) Field of Classification Search
USPC ............ 128/200.11, 200.12, 200.13, 200.14, 128/200.15, 200.16, 200.17, 200.18, 128/200.19, 200.21, 200.22, 200.23, 128/200.24, 203.12, 203.15, 205.23; 222/36, 38
See application file for complete search history.

(56) References Cited

U.S. PATENT DOCUMENTS

| | | | |
|---|---|---|---|
| 6,446,627 B1 * | 9/2002 | Bowman et al. | ........ 128/200.23 |
| 6,659,307 B1 * | 12/2003 | Stradella | ............ A61M 15/009 116/278 |
| 7,156,258 B2 | 1/2007 | Eckert | |
| 7,587,988 B2 * | 9/2009 | Bowman et al. | ............. 116/307 |
| 7,819,075 B2 | 10/2010 | Bowman | |
| 7,832,351 B2 | 11/2010 | Bonney et al. | |
| 2002/0047021 A1 | 4/2002 | Blacker et al. | |
| 2003/0209239 A1 | 11/2003 | Rand et al. | |
| 2006/0060192 A1 | 3/2006 | Lu | |
| 2007/0241025 A1 | 10/2007 | Parkes | |
| 2008/0035144 A1 | 2/2008 | Bowman et al. | |
| 2008/0156321 A1 | 7/2008 | Bowman et al. | |
| 2010/0078490 A1 * | 4/2010 | Fenlon | ........................ 235/91 R |
| 2012/0247458 A1 | 10/2012 | Lawrence | |

FOREIGN PATENT DOCUMENTS

| | | |
|---|---|---|
| CN | 101198972 A | 6/2008 |
| GB | 2320489 A | 6/1998 |
| GB | 2348928 A | 10/2000 |
| JP | 2007534378 | 11/2005 |
| WO | WO92/09324 | 6/1992 |
| WO | 199828033 | 7/1998 |
| WO | 9856444 | 12/1998 |
| WO | WO 01/28887 A1 | 4/2001 |
| WO | WO2005102430 A1 | 11/2005 |
| WO | WO2006110080 A1 | 10/2006 |
| WO | 2008015542 | 2/2008 |
| WO | WO2008/119552 A1 | 10/2008 |
| WO | WO2008121459 A1 | 10/2008 |

OTHER PUBLICATIONS

International Search Report, dated Oct. 29, 2010, International Appl. No. PCT/EP2010/004791, filed Jul. 28, 2010, IVAX Pharmaceuticals Ireland.
International Search Report, dated Nov. 9, 2010, International Appl. No. PCT/EP2010/004792, filed Jul. 28, 2010, IVAX Pharmaceuticals Ireland.
English translation of Chinese Office Action, dated Apr. 16, 2013, corresponding to counterpart application No. CN 201080041218.1.
English translation of Chinese Office Action, dated Apr. 15, 2013, corresponding to counterpart application No. CN 201080040988.4.
Entire patent prosecution history of U.S. Appl. No. 13/387,535, filed Jun. 8, 2012, entitled, "Dose Counter for a Metered-Dose Inhaler."
European Search Report dated Jan. 7, 2014 for European Patent Application No. 13004775.6.
Entire patent prosecution history of U.S. Appl. No. 13/387,508, filed Jun. 8, 2012, entitled, "Dose Counter for a Metered-Dose Inhaler," now U.S. Pat. No. 6,662,381, issued Mar. 4, 2014.
Entire patent prosecution history of U.S. Appl. Nos. 14/132,918 14/132,918, filed Dec. 18, 2013, entitled, "Dose Counter for a Metered-Dose Inhaler."
European Search Report dated Feb. 7, 2014, for European Patent Application No. 13005367.1.
Final Office Action dated Mar. 21, 2017 for U.S. Appl. No. 14/876,190, 12 pages.

* cited by examiner

Fig. 1

PRIOR ART

Fig. 2

PRIOR ART

Fig. 3

PRIOR ART

Fig. 4

PRIOR ART

DOSE COUNTER FOR A METERED-DOSE INHALER

CROSS-REFERENCE TO RELATED APPLICATIONS

This application is a U.S. National Phase Patent Application of PCT Application No. PCT/EP2010/004791, filed Jul. 28, 2010, which claims priority to U.S. Provisional Patent Application No. 61/229,830, filed Jul. 30, 2009, both of which are incorporated by reference herein in their entirety.

FIELD OF THE INVENTION

This invention relates to a dose counter suitable for inclusion in a metered-dose inhaler. The invention also relates to a metered-dose inhaler which includes the dose counter and a method of counting doses dispensed from a metered-dose inhaler.

BACKGROUND OF THE INVENTION

Metered-dose inhalers include pressurised metered-dose inhalers (of both manually operable and breath-actuated types) and dry-powder inhalers. Such metered-dose inhalers typically comprise a medicament-containing vessel and an actuator body having a drug delivery outlet. The medicament-containing vessel may be a pressurised canister containing a mixture of active drug and propellant. Such canisters are usually formed from a deep-drawn aluminium cup having a crimped ferrule which carries a metering valve assembly. The metering valve assembly is provided with a protruding valve stem which, in use, is inserted as a tight push fit into a so-called "stem block" in the body.

To actuate the conventional manually operable inhaler, the user applies a compressive force to the closed end of the canister. The internal components of the metering valve assembly are spring loaded so that a compressive force of about 15 to 30 N is required to activate the device. In response to this compressive force, the canister moves axially with respect to the valve stem by an amount varying from about 2 to 4 mm. This degree of axial movement is sufficient to actuate the metering valve and cause a metered quantity of the drug and propellant to be expelled through the valve stem. This is then released into the mouthpiece via a nozzle in the stem block. A user inhaling through the drug delivery outlet of the device at this point will thus receive a dose of the drug.

Metered-dose inhalers as described above administer an accurate dose of medicament whenever required, which is particularly useful for users whose respiratory difficulties manifest themselves suddenly. Such has been the success of these devices that they are now used throughout the world.

A more recent development is the so-called breath-actuated metered-dose inhaler which delivers a dose of drug through a mouthpiece in response to inhalation by the user. This type of arrangement is particularly convenient in circumstances where the co-ordination between user inhalation and manual depression of the aerosol canister is imperfect. For example, children sometimes lack the necessary co-ordination to achieve effective self-administration and, at times of respiratory distress, adult users may also experience poor co-ordination.

One of the drawbacks of self-administration from an inhaler, whether manually operated or breath-actuated, is that users often experience difficulty in determining when the charge in the medicament-containing vessel has nearly run out, since the contents of the medicament reservoir are typically invisible to the user. With aerosol canisters, part of the reason for this difficulty is that a surplus of propellant may remain in the canister even though the drug supply is nearly exhausted. Alternatively, the near-exhausted state may result in a surplus of drug in relation to propellant. Thus, the illusion is created that the inhaler is still capable of providing useful doses of medicament simply because the canister contains liquid. This is potentially hazardous for the user since dosing becomes unreliable and because few users routinely carry a back-up device. Many users have several different inhalers for the treatment of a variety of conditions. Others keep inhalers at a number of different locations such as at school, home, work etc. In these circumstances it is particularly difficult for the user to keep track of the amount of usage extracted from each individual inhaler apparatus.

WO 98/28033 discloses a dose counter suitable for use with the above-described metered-dose inhalers. The dose counter enables users to assess how many doses remain in the obscured canister. Such a counter can provide a warning when the inhaler nears exhaustion so that appropriate measures can be taken to avoid running out of medication. Moreover, since the dose counter has a counting resolution of one dose, it can be used for compliance monitoring, either under hospital supervision or by parents and teachers assessing compliance by children in their care. Furthermore, there are regulatory requirements for metered-dose inhalers to have a dose counter in a number of countries.

Figure 1:
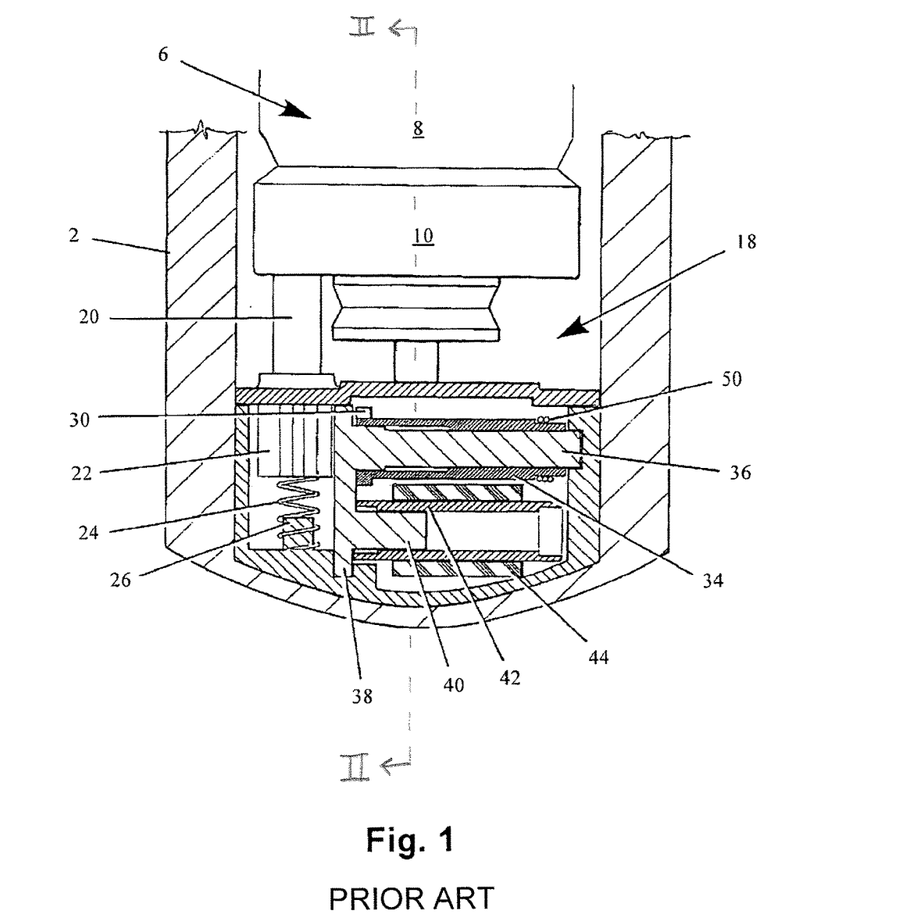
FIG. 1 is a schematic and partial sectional view of an inhaler apparatus, taken along the lines I-I in FIG. 9, showing a counter mechanism in position near the base of an inhaler actuator.
Figure 2:
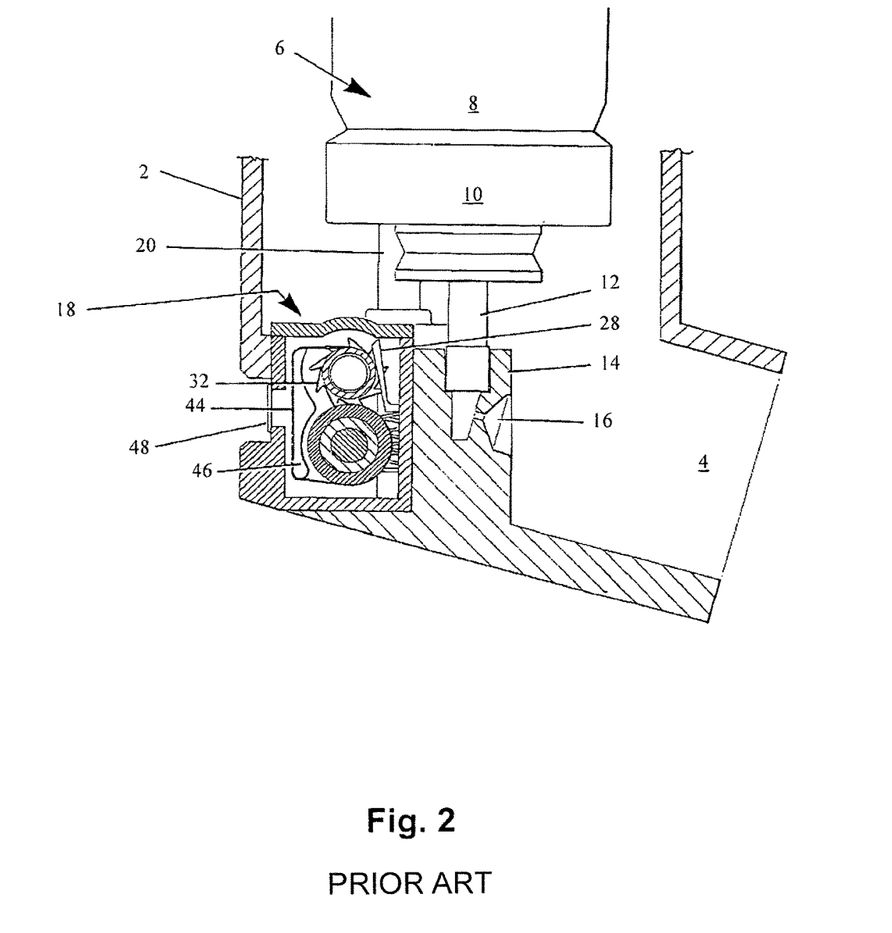
FIG. 2 is a schematic and partial sectional view of the inhaler of FIG. 1 taken along the lines II-II in FIG. 1.
Figure 3:
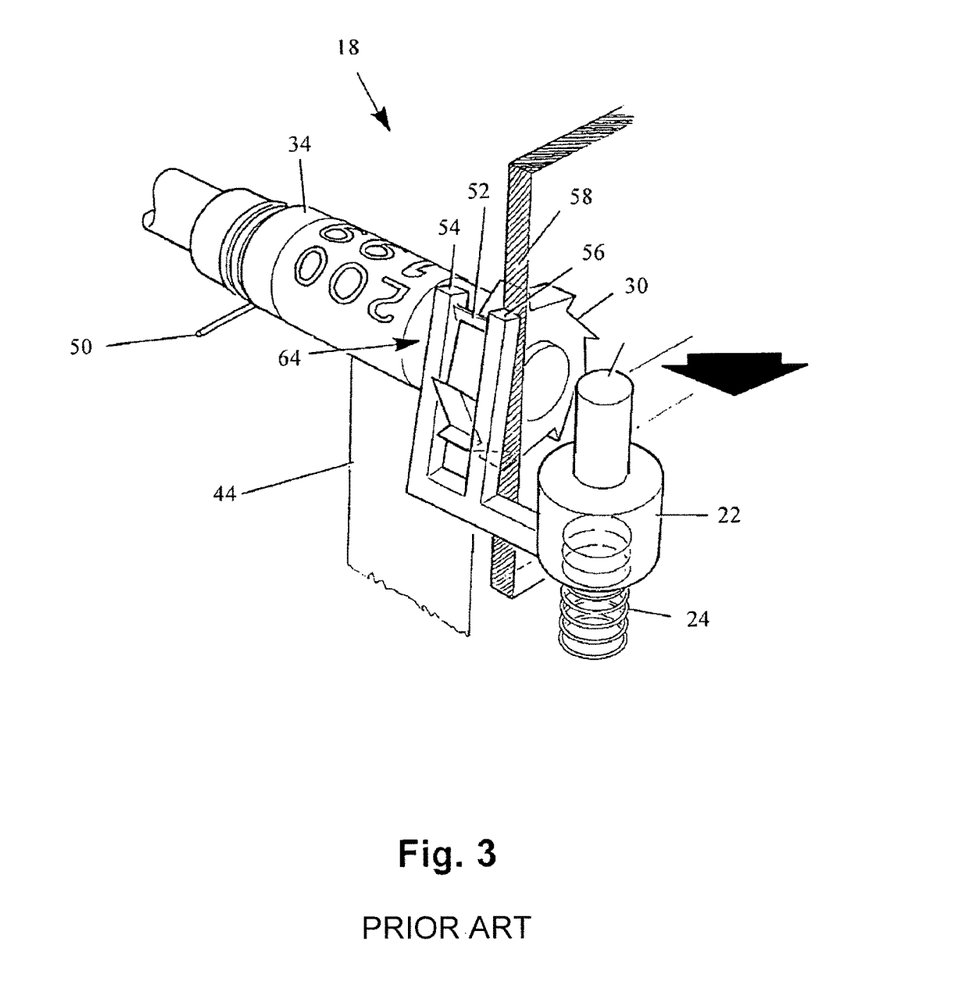
FIG. 3 is a schematic perspective view of the inhaler of FIG. 1.

FIGS. 1 to 3 reproduced herein from WO 98/28033 show the lower portion of a metered-dose inhaler. The inhaler comprises a body 2 having a drug delivery outlet 4. An aerosol canister 6 extends into the lower portion of the body 2. The aerosol canister 6 is formed from a deep-drawn aluminium cup 8 to which a ferrule 10 is attached by crimping.

The lid 10 carries a metering-valve assembly having a protruding valve stem 12, the end of which is received as a tight push fit in a stem block 14 of the body 2. Stem block 14 has a nozzle 16 communicating with the drug delivery outlet 4 so that, upon actuation of the metering-valve assembly, a charge of the drug is emitted through the nozzle 16 into the drug delivery outlet 4. Actuation of the metering-valve assembly is effected by causing downward movement of the aerosol canister 6 relative to the body 2. This may be achieved through manual pressure exerted by the user against the upturned base (not shown) of the aerosol canister 6 or by automatic depression of the aerosol canister 6 in response to user inhalation in inhalers of the breath-actuated type. The mechanism of actuation does not form part of WO 98/28033 or the present invention and will not be described in further detail. A user inhaling through the drug delivery outlet 4 when the aerosol canister 6 is depressed will receive a metered dose of the drug.

With reference to the Figures, a counter mechanism 18 includes an actuator shaft 20 moulded from a plastics material, such as nylon, the actuator shaft 20 having a boss 22 integrally formed at its base. The underside of boss 22 is formed with a blind hole which receives a compression spring 24 mounted on an upstanding spigot 26 formed on a lower element of the counter chassis.

A driver 28 for driving a rotary gear in the form of a ratchet-toothed wheel 30 is integrally moulded with boss 22 of the actuator shaft 20 and comprises a transverse hook element mounted between two arms (only one of which is visible in FIG. 2), the bases of which are conjoined to the boss 22. The transverse hook is dimensioned and oriented to engage with ratchet teeth 32 formed around the periphery of the ratchet-toothed wheel 30 to rotate it in a forward direction.

The ratchet-toothed wheel 30 is integrally moulded with a first hollow axle 34 which is rotatably supported on a first spindle 36 that projects transversely from a chassis sub-element 38. Chassis sub-element 38 also has a second spindle 40 projecting transversely therefrom on which a second hollow axle 42 is rotatably supported. A flexible tape 44 is wound around the second hollow axle 42 which serves as a supply spool and passes to the first hollow axle 34 which serves as a take-up spool (stock bobbin). A guide plate 46 forming part of the chassis sub-element 38 helps to guide the tape 44 in a smooth passage from the supply spool to the take-up spool. The surface of the tape 44 is marked with a progression of descending numbers which denote the number of doses remaining in the aerosol canister. Typically, the starting count is 200 and successive markings on the tape decrease by one. Markings on the tape actually decrease by two. The spacing between successive markings is coincident with the indexing motion of the ratchet-toothed wheel 30 so that a new number appears in a window 48 provided in the body 2 for each successive actuation.

The ratchet-toothed wheel 30 and integrally formed first hollow axle 34 are restrained from reverse rotation by a wrap-spring clutch 50 surrounding the hollow axle 34 at the end thereof remote from ratchet-toothed wheel 30. One end (not shown) of the wrap-spring clutch 50 is braced against the counter chassis. The windings of the wrap-spring clutch 50 are oriented such that rotation of the first hollow axle 34 in a forward sense is not resisted by the spring coils. However, reverse rotation of the hollow axle 34 acts so as to tighten the spring coils around it, thereby causing the first hollow axle 34 to be gripped by the internal surface of the wrap-spring clutch 50 and hence restraint from reverse rotation.

FIG. 3 shows a more detailed view of the principal elements of the dose counter 18. It will be seen that the driver 28 comprises the transverse hook 52 mounted between a pair of arms 54, 56 which are joined at their bases by a web. The web is connected to the boss 22 of the actuator shaft 20. A combined actuator and driver assembly may be integrally formed, such as from a plastics material, e.g. as nylon.

In use of the dose counter 18, depression of the canister 6 causes the ferrule 10 to engage with the actuator shaft 20, which actuator shaft 20 moves downwards against the compression spring 24. The transverse hook 52, in turn, engages with the ratchet teeth 32 of the ratchet-toothed wheel 30 which is mounted on the hollow axle 34 serving as the take-up spool for the flexible tape display 44. At the end of the hollow axle 34 remote from the ratchet-toothed wheel 30 is the clutch 50 which serves to restrain the axle 34 against reverse rotation and hence prevents reverse travel of the counter tape 44.

A control surface 58 is depicted in FIG. 3 as a see-through element so that the workings of the dose counter may be more clearly seen. The control surface 58 extends parallel to the direction of travel of the actuator shaft 20 and is located adjacent the ratchet-toothed wheel 30 at a position which marks a chordal projection across one of the wheel faces. One of the support arms 56 of the driver 28 is in sliding contact with control surface 58. This sliding contact serves to inhibit the natural tendency of the driver 28 to flex radially inwardly towards the axis of rotation of the ratchet-toothed wheel 30. By preventing such radially inward flexure, the control surface 58 restricts the engagement and disengagement of the drive 28 with the ratchet-toothed wheel 30 so that the distance by which the ratchet-toothed wheel 30 rotates is limited to one tooth pitch. This condition is observed regardless of the extent of linear travel, or stroke, of the actuator shaft 20.

Figure 4:
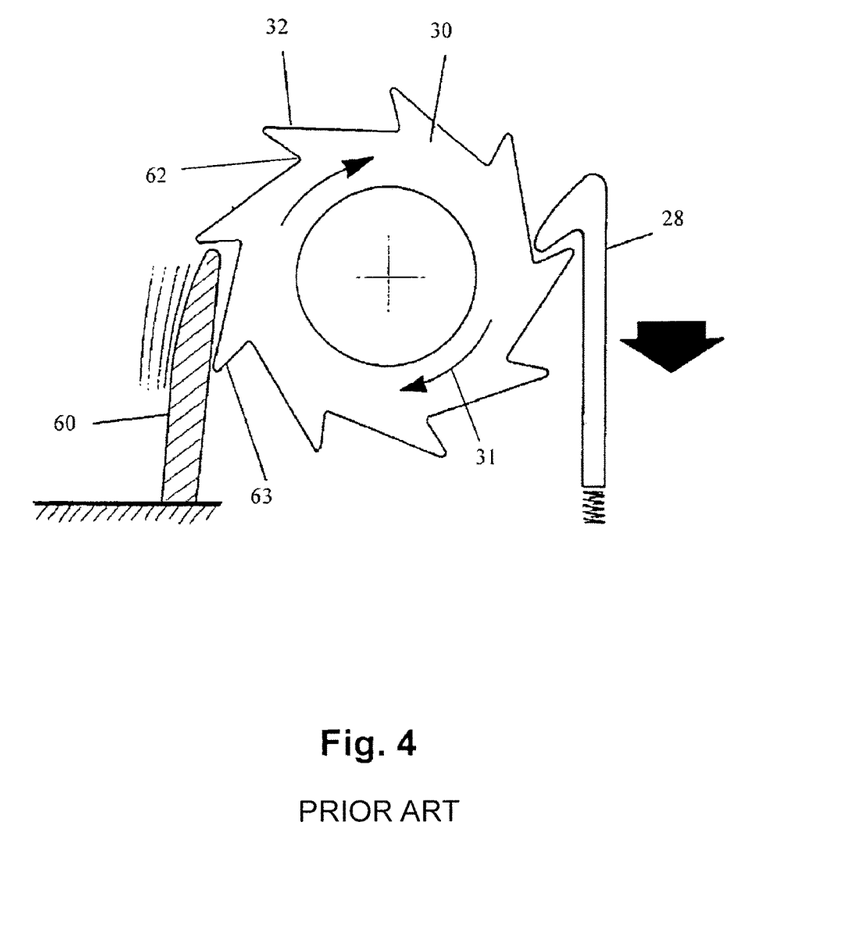
FIG. 4 is a schematic view of the dose counter of the inhaler of FIG. 1.

FIG. 4 shows a schematic view of an alternative arrangement for the ratchet-toothed wheel and driver used in the dose counter 18 described in WO 98/28033. The alternative arrangement uses a reciprocating driver 28 acting in a pushing sense to rotate a ratchet-toothed wheel 30 in the direction shown by the arrows 31. A fixed pawl 60 acts to prevent reverse rotation of the ratchet-toothed wheel 30 by engagement against the trailing edge 62 of a ratchet tooth 32. However, on forward rotation of the ratchet-toothed wheel 30 in the sense of arrows 31, the fixed pawl 60 is capable of radially outward deformation, urged by the leading edge 63 of a ratchet-tooth 32.

In this arrangement, if the ratchet-toothed wheel 30 is rotated by more than a single tooth pitch but by less than two tooth pitches for each reciprocating movement of the driver 28, there is a degree of reverse rotation until the pawl 60 becomes engaged by the trailing edge 62 (as opposed to the leading edge 63) of a ratchet tooth 32. Thus, the rotation of the ratchet-toothed wheel 30 may be described as "stepped".

The components of metered-dose inhalers are manufactured to a high technical specification. However, inevitable variations in the tolerances of the components can, in some circumstances, lead to failure of the dose counter of the type disclosed in WO 98/28033. In a known failure mode, the reciprocating stroke of the canister is insufficient to fully increment the dose counter. This may lead to undercounting, particularly where rotation of the ratchet-toothed wheel is stepped, as illustrated in FIG. 4.

Another problem relates particularly to manually operated metered-dose inhalers. In these types of inhaler, the user cannot be relied upon to repeatably actuate the inhaler with a full reciprocating stroke of the canister. Instead, the user may on some occasions release the canister immediately after the "fire point" of the metering valve, that is to say the point in the stroke at which the medicament is dispensed. This reduced stroke of the canister available for incrementing the dose counter may exacerbate the problem described above.

There is a requirement in the art, therefore, for a dose counter with a reduced failure rate. There is a particular requirement for such a dose counter which can be manufactured efficiently and incorporated into known metered-dose inhalers.

SUMMARY OF THE INVENTION

According to a first aspect of the present invention, there is provided a dose counter for counting doses of medicament dispensed by or remaining in a metered-dose inhaler, the dose counter comprising:
  a rotatably mounted gear wheel having a circular arrangement of ratchet teeth defining a root circle;
  a display coupled to the gear wheel, the display having a visible array of dose counting indicia indexable in response to rotary motion of the gear wheel; and
  an actuator mechanism having a driver for rotatably driving the gear wheel in response to the dispensation of a medicament dose, the driver being arranged to engage the ratchet teeth of the gear wheel,
  wherein the actuator mechanism comprises an actuator shaft mounted for linear movement in response to the dispensing of a dose of medicament and an engagement arm pivotally mounted to the actuator shaft and carrying the driver, the actuator shaft and the engagement arm being configured such that, in use of the dose counter for counting a dispensed dose, the travel of the driver along the root circle of the gear wheel exceeds the corresponding linear travel of the actuator shaft.

The counter of the present invention thus provides an actuator mechanism which is able to amplify the linear stroke of the actuator shaft. That is to say, the length of the travel of the driver along the root circle is greater than the length of travel of the actuator shaft.

The increased travel of the driver may be sufficient for the dose counter to be reliably incremented, even when the medicament canister is released by the user immediately after the fire point, and even when there is a large degree of accumulated variation, or tolerance stack, in the components of the inhaler. Miscounting or non-counting of doses can thereby be avoided, which in turn significantly reduces the failure rate of the dose counter. Dose counters of the type disclosed in WO 98/28033 have been found to be particularly suitable for modification according to the principles of the present invention.

In operating the dose counter, a small increase in actuating force will be required compared to dose counters of the type disclosed in WO 98/28033. For a metered-dose inhaler comprising a pressurised medicament canister, this increase in actuating force generally remains insignificant compared to the force required to overcome the internal valve spring of the canister.

The lever or linkage may be arranged such that the travel of the driver along the root circle is at least 1.1 times, preferably at least 1.15 times, and most preferably at least 1.2 times, the linear stroke of the actuator shaft. In this way, a significant amplification of the input stroke is achieved.

The pivotal mounting of the engagement arm to the actuator shaft may take one of several different forms. The engagement arm may be a separate component which is rotatably mounted to the engagement art, for example at a first (proximal) end of the engagement arm. Alternatively the engagement arm may be integrally formed with at least a portion of the actuator shaft, and the pivotal mounting provided by some form of flexure element such as a living hinge. In some embodiments a portion the actuator shaft may simply be provided with sufficient resilience to allow it to flex.

In embodiments of the dose counter the linear movement of the actuator shaft defines a longitudinal direction, which direction may be parallel with the axis of a medicament canister with which the dose counter is used. As used herein the terms "top portion" and "bottom portion" refer to portions of elements arranged at opposite ends in the longitudinal direction. The dose counter may be arranged such that the actuator shaft is spaced from the gear wheel in the lateral direction, which direction is perpendicular to the longitudinal direction. The rotational axes of the gear wheel and the pivotal axis of the engagement arm may be parallel to each other and may each be perpendicular to both the longitudinal and lateral directions.

The actuator shaft may be arranged for both a downwards stroke and an upwards stroke in response to each dispensing of a dose of medicament, i.e. reciprocating movement. In that case, the dose counter may be actuated on either the downwards or the upwards stroke of the actuator shaft. The dose counter is preferably arranged such that, in use, the driver comes into engagement with the ratchet teeth of the gear wheel at a top portion or a bottom portion of the gear wheel. The driver then rotates the gear wheel as the actuator shaft moves in the longitudinal direction to thereby increment the dose counter.

In use of the dose counter, the actuator shaft may move in a longitudinal direction and the engagement arm may pivot as the driver travels along the root circle of the gear wheel, such that the lateral spacing between the driver and the pivotal axis of the engagement arm decreases.

The dose counter may be arranged such that, in use, at the point that the driver starts to drive the ratchet teeth of the gear wheel, an imaginary line joining the driver and the pivotal axis of the engagement arm defines a chord of the root circle. The chord may define a segment having at least 5%, preferably at least 8%, and more preferably at least 10% of the area of the root circle. In this way, as the actuator shaft moves longitudinally, the driver is drawn around the gear wheel and follows a path which is longer than the path followed by the actuator shaft.

The dose counter may be arranged such that the engagement arm is shaped or configured for preventing engagement of the gear wheel by the engagement arm except by the driver, typically provided at the second (distal) end. For example, the engagement arm may be non-linear, including a bend, or a portion of the engagement arm between the proximal and distal ends may be offset from the gear wheel in a direction of the rotational axis of the gear wheel.

At least one of the actuator shaft and the engagement arm may be resiliently biased towards a starting position, the actuator shaft and/or engagement arm being displaceable against the resilient bias to actuate the dose counter. Each resilient bias may be provided by at least one of: a separate leaf spring, an integrally formed leaf spring, a compression spring and a torsion spring.

The dose counter may be provided with means to prevent reverse rotation of the gear wheel, such as a pawl arranged to engage the ratchet teeth of the gear wheel. This means may provide step-wise rotation of the gear wheel.

The driver may be carried by the second (distal) end of the engagement arm and preferably comprises a ratchet drive pawl. A control surface may be provided to regulate the position of engagement and disengagement between the driver and the gear wheel.

The display may comprise a flexible tape arranged between an indexing spool and a stock bobbin. The dose counting indicia of the display may include a unique indicium for display after each and every dose has been dispensed. The dose counting indicia may comprise at least 50 unique dose counting indicia representative of a number of doses dispensed by or remaining in the inhaler.

According to a second aspect of the present invention, there is provided a metered-dose inhaler comprising:
 a medicament canister;
 an actuator body for receiving the canister and having a medicament delivery outlet; and
 the dose counter described above.

According to a third aspect of the invention, there is provided a method of counting doses dispensed from or remaining in a metered-dose inhaler, the dose counter comprising:
 a rotatably mounted gear wheel having a circular arrangement of ratchet teeth defining a root circle;
 a display coupled to the gear wheel, the display having a visible array of dose counting indicia indexable in response to rotary motion of the gear wheel; and
 an actuator mechanism comprising an actuator shaft and an engagement arm pivotally mounted to the actuator shaft, the engagement arm carrying a driver for rotatably driving the gear wheel, the method comprising depressing a medicament canister to dispense a medicament dose and to engage and linearly displace the actuator shaft, displacement of the actuator shaft causing the driver to engage the ratchet teeth of the gear wheel to thereby rotate the ratchet wheel, wherein the travel of the driver along the root circle of the gear wheel exceeds the corresponding linear travel of the actuator shaft.

The third aspect of the invention corresponds to use of the does counter or metered-dose inhaler described above. As such, the method may include using any of the features of the dose counter described above.

BRIEF DESCRIPTION OF THE DRAWINGS

The present invention will now be described, by way of example only, with reference to the accompanying drawings, in which.

DETAILED DESCRIPTION

Dose counters of the present invention are based on that shown in FIGS. 1 to 4 described hereinabove, except that the actuator mechanism is modified. Thus, the invention generally provides a dose counter comprising a rotatably mounted gear wheel having a circular arrangement of ratchet teeth and a display coupled to the gear wheel. The display has a visible array of dose counting indicia indexable in response to rotary motion of the gear wheel. The dose counter also comprises an actuator mechanism having a driver for rotatably driving the gear wheel in response to the dispensing of a medicament dose, the driver being arranged to engage the ratchet teeth of the gear wheel. According to the invention, the actuator mechanism comprises an actuator shaft mounted for reciprocating linear movement and an engagement arm pivotally mounted to the actuator shaft and carrying the driver. The actuator shaft and the engagement arm are configured such that, in use of the dose counter, the travel of the driver along the root circle of the gear wheel exceeds the corresponding linear travel of the actuator shaft.

A dose counter according to the present invention will now be described with reference to FIGS. 5 to 8c. The actuator mechanism 118 of the dose counter is shown schematically in FIG. 5, together with the gear wheel in the form of a ratchet-toothed wheel 130. The dose counter display (not fully shown in FIG. 5) is essentially the same as that illustrated in FIGS. 1 to 3 and includes a flexible tape arranged between an indexing spool and a stock bobbin.

The ratchet-toothed wheel 130 has essentially the same configuration as that of the wheel 30 illustrated in FIGS. 1 to 4. Thus, a plurality of ratchet teeth 132 are arranged about a circular periphery of the wheel 130. The ratchet-toothed wheel 130 defines a root circle 134, indicated in broken lines in FIG. 5, which passes through the roots of the ratchet teeth 132. The ratchet-toothed wheel 130 is integrally moulded with a hollow axle (not shown) serving as the indexing spool of the display. The hollow axle is rotatably supported on a spindle that projects from the chassis of the dose counter.

The ratchet-toothed wheel 130 is restrained from reverse rotation by a fixed pawl (not shown in FIG. 5) of the type illustrated in FIG. 4. The fixed pawl also provides step-wise rotation of the ratchet-toothed wheel since, if the wheel 130 is rotated by more than a single tooth pitch but by less than two tooth pitches, there is a degree of reverse rotation until the pawl becomes engaged by the trailing edge of a ratchet tooth 132.

The actuator mechanism 118 of the dose counter according to the invention differs from the actuator mechanism shown in FIGS. 1 to 4 in the design and configuration of the actuator shaft 120. In particular, instead of merely carrying a fixed driver, the actuator shaft 120 carries a pivotally mounted, generally "L" shaped engagement arm 122 which carries the driver 124 at its distal end.

The actuator shaft 120 of the dose counter according to the invention is mounted for reciprocal linear movement in a longitudinal direction. In common with the shaft shown in FIGS. 1 and 2, a top portion (not shown) of the actuator shaft 120 is arranged for engagement by a medicament canister of the metered dose inhaler with which the dose counter is used. A bottom portion of the actuator shaft 120 is provided with a blind hole 126 which receives a compression spring (not shown) mounted on an upstanding spigot formed in the counter chassis. The compression spring serves to bias the actuator arm 120 into an upper, starting position, as shown in FIG. 5.

Figure 5:
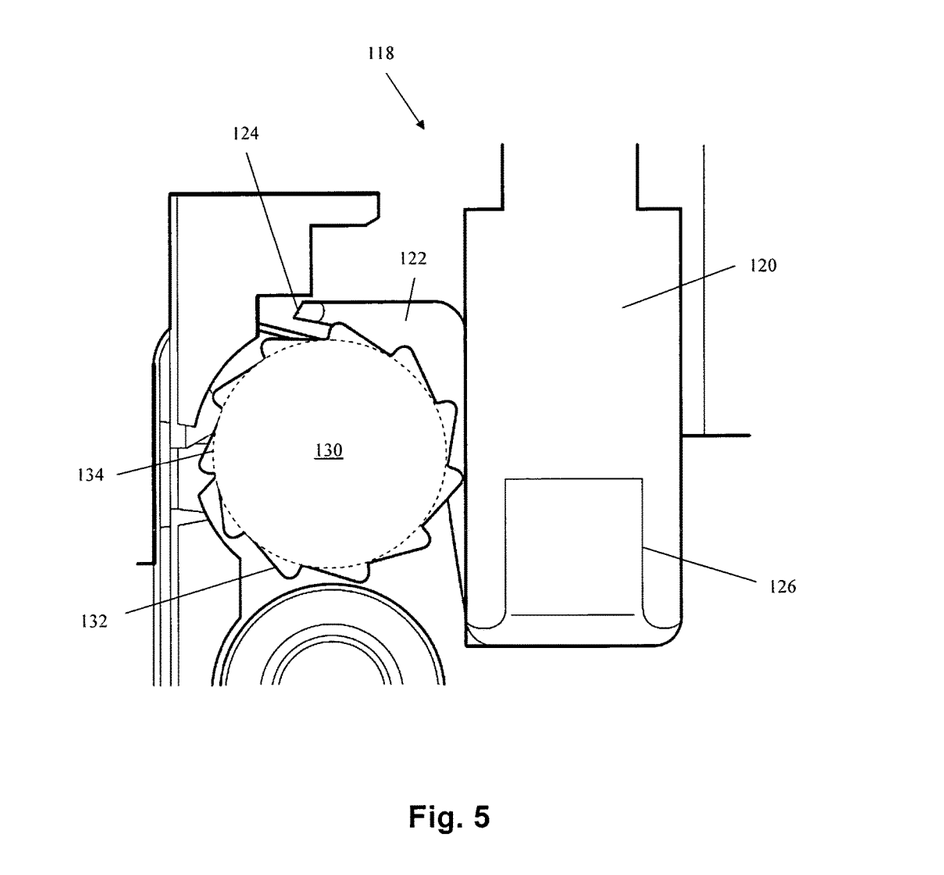
FIG. 5 is a schematic sub-assembly view of a dose counter according to the present invention.

The engagement arm 122 is pivotally mounted to a bottom portion of the actuator shaft 120, the mounting being hidden from view in FIG. 5 by the actuator shaft 120. The engagement arm 122 is biased into the position shown in FIG. 5 by a torsion spring (not shown) which is carried by the actuator shaft 120. As viewed in the figure, the engagement arm 122 can be displaced in the clockwise direction against the resilient bias. A distal end of the engagement arm 122 carries the driver 124 in the form of a ratchet drive pawl 124. The ratchet drive pawl 124 is dimensioned and orientated for suitable engagement with the ratchet teeth 132 of the ratchet-toothed wheel 130.

The ratchet-toothed wheel 130 and the actuator shaft 120 are spaced from each other in a lateral direction, which direction is perpendicular to the longitudinal direction. The rotational axis of the ratchet-toothed wheel 130 and the pivotal axis of the engagement arm 122 each extend in a transverse direction, which direction is perpendicular to both the longitudinal and lateral directions.

In the start position shown in FIG. 5, the pivotal axis of the engagement arm 122 is positioned below the ratchet-toothed wheel 130 and the driver 124 is positioned immediately above the top portion of the ratchet-toothed wheel 130. The bend in the substantially "L" shaped engagement arm 122 prevents the intermediate portion of the arm from interfering with the hub of the ratchet-toothed wheel 130. The intermediate portion of the engagement arm 122 is also offset from the ratchet-toothed wheel 130 in the transverse direction to prevent interference with the ratchet teeth 132 by the engagement arm 122, except by the driver 124.

Figure 6A:
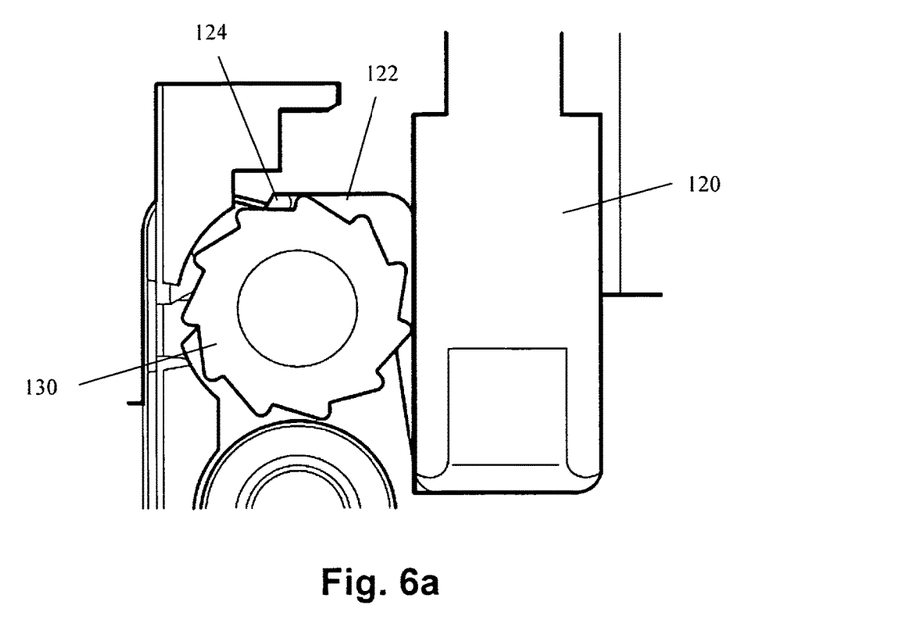
FIG. 6a is a schematic sub-assembly view of the dose counter shown in FIG. 5 for use in explaining its operation.
Figure 6B:
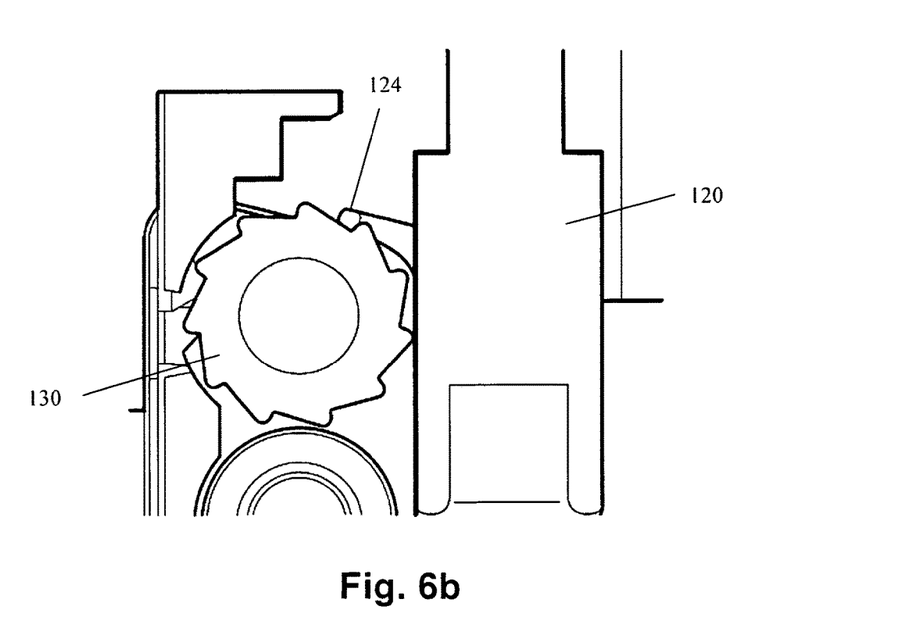
FIG. 6b is another schematic sub-assembly view of the dose counter shown in FIG. 5 for use in explaining its operation.

Use of the dose counter according to the invention for counting doses dispensed from a metered-dose inhaler will now be described with reference to FIGS. 6a and 6b. FIGS. 6a and 6b are schematic views showing the same components that are illustrated in FIG. 5. The other components of the metered-dose inhaler and the dose counter are omitted for clarity.

The metered-dose inhaler is actuated by the user applying a manual compressive force to the closed end of a medicament canister (not shown). In response to this compressive force, the canister moves axially downwards with respect to its valve stem by an amount varying from about 2 to 4 mm. Approximately 2 mm of displacement is required to fire the valve and dispense a dose of medicament. After the medicament has been dispensed, the user releases the compressive force and the canister returns to its starting position under the action of the internal valve spring.

The dose counter is driven by the reciprocating linear movement of the canister as the medicament dose is dispensed.

The downwards movement of the medicament canister during the dispensing of a medicament dose causes the ferrule of the canister to engage with and linearly displace the actuator shaft 120 downwards. The displacement of the actuator shaft 120 also causes the engagement arm 122, and the driver 124 it carries, to move downwards by a short distance until the driver 124 engages the ratchet teeth 132 formed on the top portion of the ratchet-toothed wheel 130, as shown in FIG. 6a. At this point, further downwards displacement of the actuator shaft 120 draws the driver 124 around the root circle 134 of the ratchet-toothed wheel 130, thereby rotating the ratchet-toothed wheel 130, as shown in FIG. 6b. As the driver 124 is drawn around the ratchet-toothed wheel 130 the engagement arm 122 pivots towards the actuator shaft 120.

The driver 124 rotates the ratchet-toothed wheel 130 by slightly more than a single tooth pitch. Following disengagement of the driver 124, at the end of the downwards stroke of the actuator shaft 120, there is a small degree of reverse rotation of the ratchet-toothed wheel 130 until the fixed pawl (not shown) abuts the trailing edge of one of the ratchet teeth 132 of the ratchet-toothed wheel 130, at which point the wheel 130 (and thus the display) is indexed by exactly one tooth pitch.

Figure 7A:
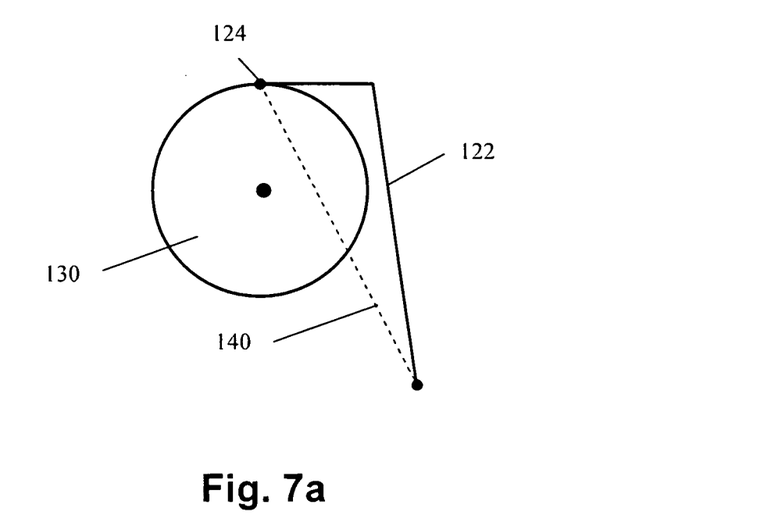
FIG. 7a is a diagram for use in explaining the principle of operation of the dose counter shown in FIG. 5.
Figure 7B:
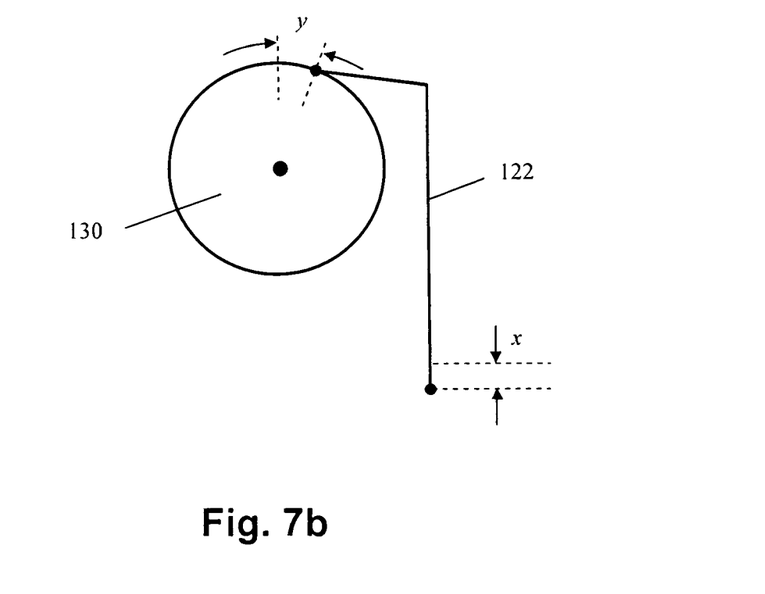
FIG. 7b is another diagram for use in explaining the principle of operation of the dose counter shown in FIG. 5.

The engagement arm 122 and the ratchet-toothed wheel 130 are schematically shown in isolation in FIGS. 7a and 7b, which are diagrams for explaining the operation of the dose counter shown in FIG. 5. The ratchet-toothed wheel 130 is represented in the Figures by its root circle, which is a line passing through the roots of the ratchet teeth 132 of the ratchet-toothed wheel 130. FIG. 7a shows the relative positions of the engagement arm 122 and the ratchet-toothed wheel 130 at the point of engagement therebetween, and prior to actuation of the dose counter. FIG. 7b shows the relative positions of the engagement arm 122 and the ratchet-toothed wheel 130 at the point of disengagement therebetween, and after actuation of the dose counter.

It will be seen in FIG. 7a that a line 140 between the pivotal axis of the engagement arm 122 and the driver 124 defines a chord of the root circle of the ratchet-toothed wheel 130. The chord defines a segment having at least 10% of the area of the root circle.

In the transition from the position shown in FIG. 7a to the position shown in FIG. 7b the actuator shaft (not shown), and thus the pivotally mounted end of the engagement arm 122, is displaced linearly downwards by a distance x. In response to this displacement of the actuator shaft 122, the driver 124 is drawn around the root circle of the ratchet-toothed wheel 130 by a distance y, which distance is greater than x. In this way, the actuator mechanism 118 serves to amplify the linear stroke of the medicament canister, thereby providing the driver 124 with increased travel.

By amplifying the linear input stroke, the length of the stroke available for indexing the ratchet-toothed wheel 130 is increased as compared to the dose counter of the type shown in FIGS. 1 to 4. This reduces the risk of miscounting, particularly undercounting and, in turn, reduces the failure rate of the dose counter.

The amplification of the linear input stroke is particularly advantageous for manually operated metered-dose inhalers, since the linear input stroke with this type of inhaler may be as small as 1.5 mm when the medicament canister is released immediately after the fire point of the valve has been reached.

The amplification of the linear input stroke can also reduce the risk of miscounting due to accumulated tolerance stacks and lost motion, as will be explained with reference to FIGS. 8a to 8c.

Figure 8A:
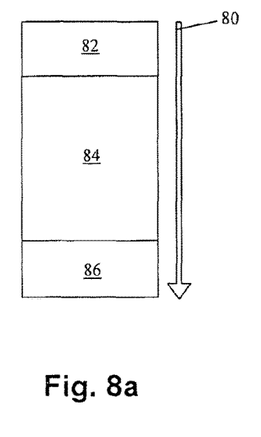
FIG. 8a is a graphical representation of the medicament canister travel during actuation of a metered-dose inhaler.

FIG. 8a is a graphical representation of the travel 80 of the medicament canister of a first inhaler having a working dose counter of the type shown in FIGS. 1 to 4. A first portion of the travel 82 takes up the accumulated tolerances of the manufactured components and any lost motion. A second portion of the travel 84 is the travel required to increment the dose counter. A third portion of the travel 86 is "excess" travel which would have been available had the accumulated tolerances or lost motion been greater.

Figure 8B:
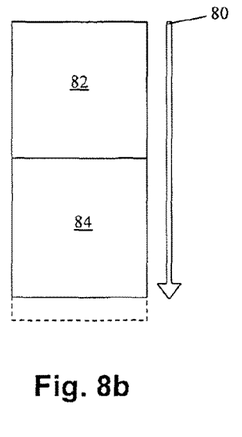
FIG. 8b is another graphical representation of the medicament canister travel during actuation of a metered-dose inhaler.

FIG. 8b is a graphical representation of the travel 80 of the medicament canister of a second inhaler having a non-working (failed) dose counter of the type shown in FIGS. 1 to 4. The total canister travel 80 is the same as that for the first inhaler shown in FIG. 8a. Again, a first portion of the travel 82 takes up the accumulated tolerances of the manufactured components and any lost motion. The accumulated tolerances and lost motion are significantly greater in the second inhaler than they were in the first inhaler, so that the first portion of the travel 82 is correspondingly greater. A second portion of the travel 84 is the travel required to increment the dose counter, and this is the same as that shown in FIG. 8a for the first inhaler. However, there is insufficient remaining canister travel 80 to increment the dose counter, which causes the dose counter to fail.

Figure 8C:
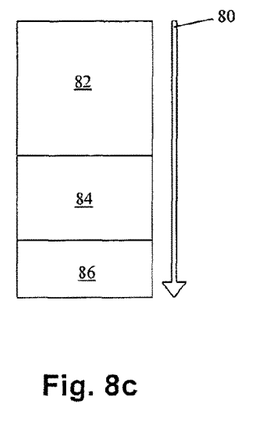
FIG. 8c is still another graphical representation of the medicament canister travel during actuation of a metered-dose inhaler.

FIG. 8c is a graphical representation of the travel 80 of the medicament canister of a third inhaler having the dose counter according to the invention shown in FIG. 5. The total canister travel 80 is the same as that for the first and second inhalers shown in FIGS. 8a and 8b. Again, a first portion of the travel 82 takes up the accumulated tolerances of the manufactured components and any lost motion. The accumulated tolerances and lost motion are the same as those of the second inhaler which led to failure of the second inhaler's dose counter. A second portion of the travel 84 is the travel required to increment the dose counter. This second portion of the travel 84 is significantly less than it is for the first and second inhalers shown in FIGS. 8*a* and 8*b*, since the second portion of the travel 84 is amplified by the dose counter. Consequently, there is sufficient remaining canister travel 80 to increment the dose counter and the dose counter does not fail. A third portion of the travel 86 is the "excess" travel which would have been available had the accumulated tolerances or lost motion been even greater.

Thus, it will be seen that amplification of the linear stroke of the medicament canister can lead to a reduction in failures caused by excessive accumulated tolerances and lost motion.

Amplification of the linear stroke of the medicament canister according to the principles of the present invention may lead to a small increase in the force with which the medicament canister must be depressed. The force required for operating the dose counter, however, generally remains small compared to the force that is required to overcome the canister's internal valve spring.

Figure 9:
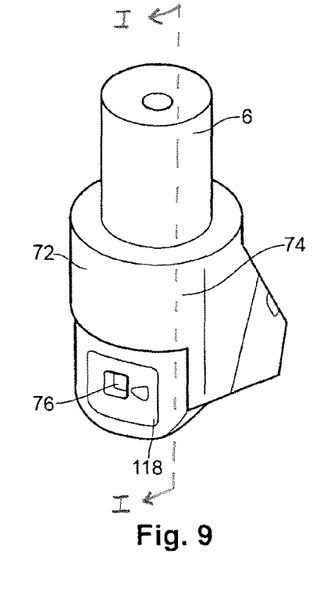
FIG. 9 is a view of a metered-dose inhaler according to the invention.

The present invention further provides a metered-dose inhaler 72 as shown in FIG. 9. The inhaler comprises a medicament canister 6, an actuator body 74 for receiving the canister 6 and having a medicament delivery outlet, and the dose counter as described hereinabove. The actuator body 74 has a window 76 for viewing the display. In a preferred embodiment the actuator body 74 comprises a sump, and preferably a smooth rounded sump. The rounded sump may have a substantially cylindrical upper portion and a substantially hemi-spherical lower portion. By providing a smooth sump the internal surfaces are sufficiently free of protrusions so that during normal use medicament will not substantially adhere thereto.

The medicament canister 6 may contain a medicament in the form of an aerosol. The medicament may be any medicament that is suitable to be delivered to a patient via a metered-dose inhaler. In particular medicaments for the treatment of a wide variety of respiratory disorders are delivered in this manner including anti-allergic agents (e.g. cromoglycate, ketotifen and nedocromil), anti-inflammatory steroids (e.g. beclomethasone dipropionate, fluticasone, budesonide, flunisolide, ciclesonide, triamcinolone acetonide and mometasone furoate); bronchodilators such as: [beta]2-agonists (e.g. fenoterol, formoterol, pirbuterol, reproterol, salbutamol, salmeterol and terbutaline), non-selective [beta]-stimulants (e.g. isoprenaline), and xanthine bronchodilators (e.g. theophylline, aminophylline and choline theophyllinate); and anticholinergic agents (e.g. ipratropium bromide, oxitropium bromide and tiotropium).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

For example, the dose counter described hereinabove is configured to actuate the dose counter on the forward (downwards) stroke of a medicament canister. Dose counters according to the invention may alternatively be configured to actuate the dose counter of the reverse (upwards) stroke.

The invention claimed is:

1. A dose counter for counting doses of medicament dispensed by or remaining in a metered-dose inhaler, the dose counter comprising:
a rotatably mounted gear wheel having a circular arrangement of ratchet teeth defining a root circle;
a display coupled to the gear wheel, the display having a visible array of dose counting indicia indexable in response to rotary motion of the gear wheel; and
an actuator mechanism having a driver for rotatably driving the gear wheel in response to the dispensation of a medicament dose, the driver being arranged to engage the ratchet teeth of the gear wheel, wherein the actuator mechanism comprises an actuator shaft mounted for linear movement in response to the dispensing of a dose of medicament and an engagement arm pivotally mounted to the actuator shaft and carrying the driver, the engagement arm being configured to initially travel linearly along with the actuator shaft until the driver contacts the ratchet teeth of the gear wheel, and, then pivot while the driver travels along the root circle of the gear wheel to thereby rotate the gear wheel,
the actuator shaft and the engagement arm being configured such that, in use of the dose counter for counting a dispensed dose, the travel of the driver along the root circle of the gear wheel exceeds the corresponding linear travel of the actuator shaft,
wherein when the driver engages the gear wheel an imaginary line joining the driver and a pivotal axis of the engagement arm comprises a chord of the root circle.

2. A dose counter according to claim 1, wherein the chord defines a segment having at least 5%, of the area of the root circle.

3. A dose counter according to claim 1, wherein, in use, the actuator shaft moves in a longitudinal direction and the engagement arm pivots such that a lateral spacing between the driver and the pivotal axis of the engagement arm decreases.

4. A dose counter according to claim 3, wherein either:
the engagement arm includes a curved portion; or
a portion of the engagement arm is offset from the gear wheel in a direction of the rotational axis of the gear wheel, for preventing engagement of the gear wheel by the engagement arm except by the driver.

5. A dose counter according to claim 1, wherein the driver is carried by a distal end of the engagement arm.

6. A dose counter as claimed in claim 1, wherein at least one of the actuator shaft and the engagement arm is resiliently biased towards a starting position, the actuator shaft and/or engagement arm being displaceable against a resilient bias for actuating the dose counter.

7. A dose counter as claimed in claim 1, wherein an end of the actuator shaft is arranged for direct engagement by a medicament canister of the metered dose inhaler.

8. A dose counter as claimed in claim 1, wherein the actuator shaft and the engagement arm are configured such that, in use of the dose counter, travel of the driver along the root circle is at least 1.1 times the linear travel of the actuator shaft.

9. A dose counter as claimed in claim 1, further comprising means for preventing reverse rotation of the gear wheel.

10. A dose counter as claimed in claim 9, wherein the means for preventing reverse rotation comprises at least one pawl arranged to engage the ratchet teeth of the gear wheel.

11. A dose counter according to claim 1, wherein the driver comprises a ratchet drive pawl.

12. A dose counter according to claim 1, wherein the display comprises a flexible tape arranged between an indexing spool and a stock bobbin.

13. A metered-dose inhaler comprising:
a medicament canister;
an actuator body for receiving the canister and having a medicament delivery outlet; and
the dose counter as claimed in claim 1.

14. A method of counting doses dispensed from or remaining in a metered-dose inhaler, the dose counter including:
a rotatably mounted gear wheel having a circular arrangement of ratchet teeth defining a root circle;
a display coupled to the gear wheel, the display having a visible array of dose counting indicia indexable in response to rotary motion of the gear wheel; and
an actuator mechanism including an actuator shaft and an engagement arm pivotally mounted to the actuator shaft, the engagement arm carrying a driver for rotatably driving the gear wheel,
said method comprising depressing a medicament canister to dispense a dose and to engage and linearly displace the actuator shaft, displacement of the actuator shaft causing the engagement arm to initially travel linearly along with the actuator shaft until the driver contacts the ratchet teeth of the gear wheel, and then pivot while the driver travels along the root circle of the gear wheel to thereby rotate the gear wheel, wherein the travel of the driver along the root circle of the gear wheel exceeds a corresponding linear travel of the actuator shaft,
wherein when the driver engages the gear wheel an imaginary line joining the driver and a pivotal axis of the engagement arm comprises a chord of the root circle.

15. The dose counter according to claim 1, wherein displacement of the actuator shaft causes the engagement arm to linearly travel without rotating until the driver contacts the ratchet teeth of the gear wheel.

16. The method according to claim 14, wherein displacement of the actuator shaft causes the engagement arm to linearly travel without rotating until the driver contacts the ratchet teeth of the gear wheel.

17. The dose counter according to claim 1, wherein the engagement arm is configured to pivot about a pivot axis and the driver is configured to pull the ratchet teeth of the gear wheel towards the pivot axis as the driver travels along the root circle of the gear wheel.

18. The method according to claim 14, wherein the engagement arm is configured to pivot about a pivot axis and the driver pulls the ratchet teeth of the gear wheel towards the pivot axis as the driver travels along the root circle of the gear wheel.

19. The dose counter according to claim 1, wherein the gear wheel is configured to rotate about a gear wheel axis and a portion of the engagement arm is offset from the gear wheel along the gear wheel axis.

20. The method according to claim 14, wherein the gear wheel is configured to rotate about a gear wheel axis and a portion of the engagement arm is offset from the gear wheel along the gear wheel axis.

* * * * *